US00PP22204P2

(12) United States Plant Patent
Lekkerkerk

(10) Patent No.: US PP22,204 P2
(45) Date of Patent: Oct. 18, 2011

(54) ***GERBERA* PLANT NAMED 'LEKGERYEL'**

(50) Latin Name: *Gerbera×hybrida*
Varietal Denomination: Lekgeryel

(76) Inventor: Cornelis Gijsbertus Lekkerkerk, Pijnacker (NL)

( * ) Notice: Subject to any disclaimer, the term of this patent is extended or adjusted under 35 U.S.C. 154(b) by 0 days.

(21) Appl. No.: 12/803,796

(22) Filed: Jul. 7, 2010

(51) Int. Cl.
*A01H 5/00* (2006.01)

(52) U.S. Cl. ..... Plt./357

(58) Field of Classification Search ..... Plt./357
See application file for complete search history.

*Primary Examiner* — Annette Para
(74) *Attorney, Agent, or Firm* — Audrey Charles

(57) ABSTRACT

A new and distinct cultivar of *Gerbera* plant named 'Lekgeryel', characterized by its double-type, medium yellow-colored flowers, medium green-colored foliage, and moderately vigorous, compact-upright growth habit, is disclosed.

1 Drawing Sheet

Latin name of genus and species of plant claimed: *Gerbera×hybrida.*

Variety denomination: 'Lekgeryel'.

BACKGROUND OF THE INVENTION

The present invention relates to a new and distinct cultivar of *Gerbera* plant botanically known as *Gerbera×hybrida* and hereinafter referred to by the cultivar name 'Lekgeryel'.

The new cultivar originated in a controlled breeding program in Pijnacker, The Netherlands during May 2007. The objective of the breeding program was the development of *Gerbera* cultivars that are freely flowering with large flowers.

The new *Gerbera* cultivar is the result of cross-pollination. The female (seed) parent of the new cultivar is the proprietary *Gerbera×hybrida* breeding line designated HEAF 187, not patented, characterized by its single-type, medium yellow-colored flowers, medium green-colored foliage, low growth vigor, and upright growth habit. The male (pollen) parent of the new cultivar is the proprietary *Gerbera×hybrida* breeding line designated AF 621, not patented, characterized by its double-type, medium yellow-colored flowers, medium green-colored foliage, and vigorous, upright growth habit. The new cultivar was discovered and selected as a single flowering plant within the progeny of the above stated cross-pollination during May 2008 in a controlled environment at Pijnacker, The Netherlands.

Asexual reproduction of the new cultivar by tissue culture propagation in a controlled environment since May 2008 at Pijnacker, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Lekgeryel' as a new and distinct cultivar of *Gerbera* plant:

1. Double-type, medium yellow-colored flowers;
2. Medium green-colored foliage; and
3. Moderately vigorous, compact-upright growth habit.

Plants of the new cultivar differ from plants of the female parent primarily in flower type and growth vigor from plants of the male parent primarily in growth vigor and habit.

Of the many commercially available *Gerbera* cultivars, the most similar in comparison to the new cultivar is Revolution 'Mega Yellow', not patented. However, in side by side comparisons, plants of the new cultivar differ from plants of Revolution 'Mega Yellow' in at least the following characteristics:

1. Plants of the new cultivar are more double flowering than plants of Revolution 'Mega Yellow'; and
2. Plants of the new cultivar are more vigorous than plants of Revolution 'Mega Yellow'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Lekgeryel'. The plants were grown in 14 cm pots for approximately 11 weeks in a greenhouse at Pijnacker, The Netherlands.

DETAILED BOTANICAL DESCRIPTION

Figure 1:
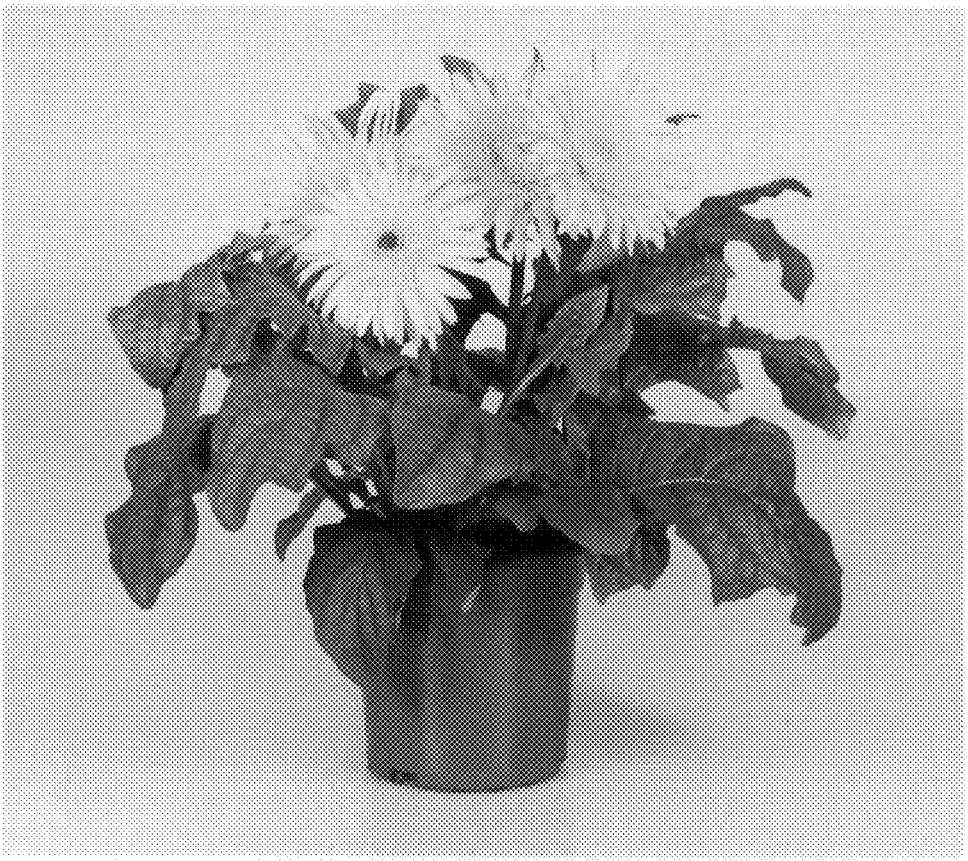
FIG. 1 illustrates a side view of the overall growth and flowering habit of 'Lekgeryel'.
Figure 2:
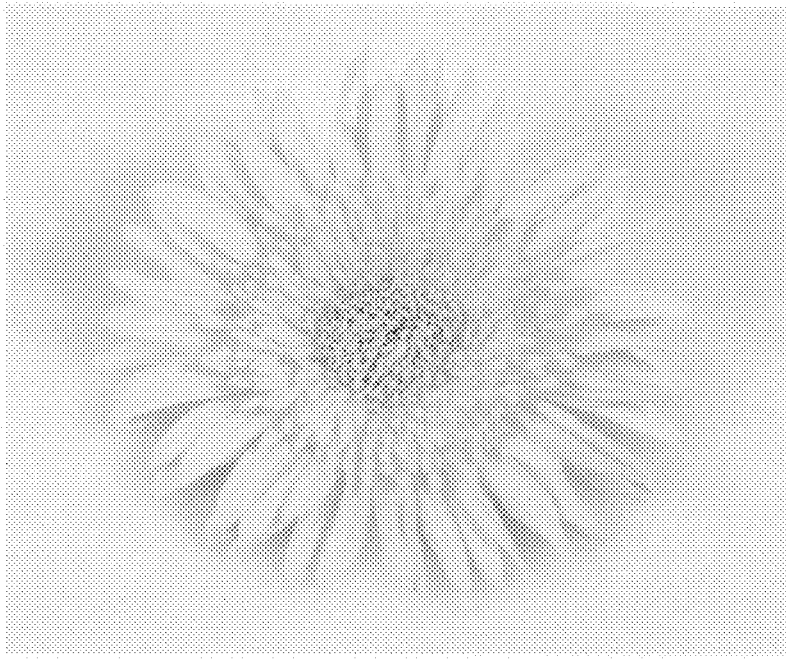
FIG. 2 illustrates a close-up view of an individual inflorescence of 'Lekgeryel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in August 2009 under natural light conditions in Pijnacker, The Netherlands.

The following descriptions and measurements describe plants produced from tissue culture plantlets and grown in a glass-covered greenhouse under conditions comparable to those used in commercial practice. The plants were grown in Pijnacker, The Netherlands in 14 cm pots for approximately 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Gerbera×hybrida* cultivar Lekgeryel.

Parentage:

*Female parent.*—Proprietary *Gerbera×hybrida* breeding line designated HEAF 187, not patented.

*Male parent.*—Proprietary *Gerbera×hybrida* breeding line designated AF 621, not patented.

Propagation:

*Type cutting.*—Tissue culture plantlets.

*Time to initiate roots in vitro.*—Approximately 7 to 9 days.

*Time to produce a tissue culture plantlet.*—Approximately 35 to 49 days.

*Root description.*—Fibrous.

*Rooting habit.*—Freely branching.

Plant description:

*Commercial crop time.*—Approximately 10 to 12 weeks from a tissue culture plantlet to finish in a 14 cm pot.

*Growth habit and general appearance.*—Moderately vigorous, compact-upright.

*Size.*—Height from soil level to top of plant plane: Approximately 32.0 cm. Height from soil level to top of foliage: Approximately 27.0 cm. Width: Approximately 32.0 cm.

*Branching habit.*—No lateral branching, basal rosette.

Foliage description:

*General description.*—Fragrance: None. Form: Simple, arising from a basal rosette.

*Leaves.*—Shape: Elliptical. Margin: Deeply incised, dentate. Apex: Acute. Base: Attenuate. Venation pattern: Pinnate, reticulate. Length of mature leaf: Approximately 28.0 cm. Width of mature leaf: Approximately 8.0 cm. Texture of upper and lower surfaces: Glandular pubescent. Gland color: 135A. Color of upper surface of young and mature foliage: 137A with venation of 138B. Color of lower surface of young foliage: 138A with venation of 138B. Color of lower surface of mature foliage: 138A with venation of 137B.

*Petiole.*—Length: Approximately 9.0 cm. Diameter: Approximately 3.5 mm. Texture: Glandular pubescent. Gland color: 145A, transparent. Color: 145A.

Flowering description:

*Flowering habit.*—'Lekgeryel' is freely flowering under outdoor growing conditions with substantially continuous blooming from spring through autumn and year-round in greenhouse environment.

*Lastingness of individual flower on the plant.*—Approximately 30 days.

Inflorescence description:

*General description.*—Type: Double, composite. Aspect: Facing upward and outward. Arrangement: Positioned above foliage. Quantity of fully open inflorescences per plant: Approximately 7. Quantity of developing inflorescences per plant: Approximately: 3. Fragrance: None. Length or height: Approximately 3.0 cm. Width: Approximately 12.0 cm.

*Peduncle.*—Strength: Strong. Aspect: Erect. Length: Approximately 25.0 cm. Diameter: Approximately 7.5 mm. Texture: Glandular pubescent. Gland color: Colorless, transparent. Color: 144A.

*Bud.*—Rate of opening: Generally takes 5 to 10 days for bud to progress from first color to fully open flower. Shape: Round. Length: Approximately 1.0 cm. Width: Approximately 3.0 cm. Petal color: 12A.

*Ray florets.*—Quantity per inflorescence: Approximately 60 outer ray florets and 160 inner ray florets. Shape: Lanceolate to narrow elliptic. Appearance: Iridescent. Margin: Entire. Apex: Acute. Base: Attenuate. Length of outer ray florets: Approximately 6.0 cm. Width of outer ray florets: Approximately 6.0 mm. Length of inner ray florets: Approximately 5.0 cm. Width of inner ray florets: Approximately 7.0 mm. Texture of upper and lower surfaces: Glabrous. Color of upper surface when fully open: 12A. Color of lower surface when fully open: 12A.

*Disc florets.*—Disc diameter: Approximately 2.4 cm. Quantity per inflorescence: Approximately 300. Arrangement: Spirally arranged in center of inflorescence. Shape: Tubular. Margin of free portion: Entire. Apex: Five acute tips. Base: Fused into a tube. Length: Approximately 1.1 cm. Diameter at apex: Approximately 1.0 to 2.0 mm. Diameter at base: Less than 1.0 mm. Color: 172B to 172C.

*Receptacle.*—Shape: Cone. Height: approximately 1.0 cm. Diameter at base: Approximately 2.1 cm. Color: 145D.

*Involucre.*—Height: Approximately 1.0 cm. Diameter: Approximately 2.0 cm.

*Phyllaries.*—Quantity per inflorescence: Approximately 80. Arrangement: Imbricate in several whorls. Shape: Lanceolate. Margin: Entire. Apex: Attenuate. Base: Fused. Texture of upper and lower surfaces: Glandular pubescent. Gland color: Colorless, transparent. Color of upper surface: 137D. Color of lower surface: 137C.

*Reproductive organs.*—Androecium: Present on disc florets and some imperfect stamens on the inner ray florets. Stamen quantity: Approximately 2 per flower. Anther shape: Oblong. Anther length: Approximately 2.0 mm. Anther color: 151D. Pollen amount: Sparse. Pollen color: 155D. Gynoecium: Present on ray and disc florets. Pistil quantity: 1 per flower. Pistil length: Approximately 1.0 cm. Stigma shape: Split heart shape. Stigma length: Approximately 1.0 mm. Stigma color: 2D. Style length: Approximately 8.0 mm. Style color: 2C. Ovary length: Approximately 1.5 mm. Ovary texture: Glabrous. Ovary color: 155A.

Seed and fruit production: Neither seed nor fruit production has been observed.

Disease and pest resistance: Resistance to pathogens and pests common to *Gerbera* has not been observed.

What is claimed is:

1. A new and distinct cultivar of *Gerbera* plant named 'Lekgeryel', substantially as herein shown and described.

* * * * *